US007005426B2

(12) United States Patent
Lu et al.

(10) Patent No.: US 7,005,426 B2
(45) Date of Patent: Feb. 28, 2006

(54) FOLIC ACID-POLYSACCHARIDE COMPLEX, ITS PREPARATION METHOD AND PHARMACEUTICAL COMPOSITION CONTAINING THE SAME AS ACTIVE COMPONENT

(75) Inventors: Weiyue Lu, Shanghai (CN); Min Liu, Shanghai (CN); Jun Pan, Shanghai (CN)

(73) Assignee: Shanghai Pharmco Research, Inc., Shanghai (CN)

( * ) Notice: Subject to any disclaimer, the term of this patent is extended or adjusted under 35 U.S.C. 154(b) by 174 days.

(21) Appl. No.: 10/274,854

(22) Filed: Oct. 17, 2002

(65) Prior Publication Data

US 2003/0125302 A1 Jul. 3, 2003

Related U.S. Application Data

(63) Continuation of application No. PCT/CN01/00555, filed on Apr. 16, 2001.

(30) Foreign Application Priority Data

Apr. 17, 2000 (CN) ........................................ 00115400 A
May 18, 2000 (CN) ........................................ 00115752 A

(51) Int. Cl.
A61K 31/715 (2006.01)
A61K 31/721 (2006.01)
C08B 37/00 (2006.01)
C08B 37/02 (2006.01)

(52) U.S. Cl. .............................. 514/54; 514/59; 514/58; 514/56; 536/55.1; 536/51; 536/46; 536/21; 436/505

(58) Field of Classification Search ................... 514/54, 514/59, 58, 56; 536/55.1, 51, 46, 21, 123.12; 436/505
See application file for complete search history.

(56) References Cited

U.S. PATENT DOCUMENTS

| 4,046,722 A | 9/1977 | Rowland | 260/6 |
|---|---|---|---|
| 4,857,505 A | 8/1989 | Arendt | 514/2 |
| 5,045,535 A | 9/1991 | Mang | 514/57 |
| 5,455,236 A | 10/1995 | Muller et al. | |
| 5,547,668 A | 8/1996 | Kranz et al. | 424/181.1 |
| 5,554,386 A | * 9/1996 | Groman et al. | 424/488 |

FOREIGN PATENT DOCUMENTS

| EP | 383 170 | 8/1990 |
|---|---|---|
| GB | 1201014 | 8/1970 |
| JP | 59-152327 | 8/1984 |
| JP | 61-207237 | 3/1985 |
| WO | WO 90/12096 | 10/1990 |
| WO | WO 92/11037 | * 7/1992 |

OTHER PUBLICATIONS

Onishi et al. (Chemical and Pharmaceutical Bulletin, (Jun. 1986) 34(6), 2561–7).*
Dang et al. (Cancer Research (Apr. 1, 1994) 54 (7) 1729–35).*
Dang et al. (Cancer Research (Apr. 1, 1994) 54 (7) 1729–35) (abstract sent).*
Chinese Patent No. 1,081,688 (Abstract only).
"Measurement of endosome pH following folate receptor-mediated endocytosis" Robert J. Lee, Susan Wang, Phillip S. Low, *Biochimica et Biophysica Acta 1312*(1996) 237–242.
"Iron Oxide Nanoparticles as Magnetic Resonance Contrast Agent for Tumor Imaging via Folate Receptor-targeted Delivery", Hoon Choi, PhD et al., *Academic Radiology, vol. 11, No. 9*, (2004).
XP–002309369, Biosis database, "Tetratogenicity Studies with Methotrexate Aminopterin and Acetyl Salicylic–Acid in Domestic Cats", Tetratology 14(1):21–27 (1976) (Abstract).

* cited by examiner

*Primary Examiner*—James O. Wilson
*Assistant Examiner*—Michael C. Henry
(74) *Attorney, Agent, or Firm*—Darby & Darby

(57) ABSTRACT

The present invention relates to folic acid-polysaccharide complexs and method of preparation thereof, more particularly relates to folic acid-Dextran complexs, method of preparation thereof, pharmaceutical compositions having said complex as active component and uses of said composition in therapy of tumors. The folic acid-polysaccharide complexs of the present invention have general formula of: $(X)_n$—Y, wherein X is identical or different, and is selected from folic acid, derivatives of folic acid and other substances that can enter into cell via the pathway of folic acid receptor; Y is polysaccharide; $n \geq 1$.

17 Claims, 8 Drawing Sheets

FOLIC ACID-POLYSACCHARIDE COMPLEX, ITS PREPARATION METHOD AND PHARMACEUTICAL COMPOSITION CONTAINING THE SAME AS ACTIVE COMPONENT

This is a continuation of international application Ser. No. PCT/CN01/00555, filed Apr. 16, 2001, the entire disclosure of which is hereby incorporated by reference.

TECHNICAL FIELD OF THE INVENTION

The present invention relates to folic acid-polysaccharide complexes and method for preparation thereof, more particularly relates to folic acid-Dextran complexs, method for preparation thereof, pharmaceutical compositions having said complex as active component and uses of said composition in therapy of tumor.

BACKGROUND OF THE INVENTION

After the concept of specific folic acid binding protein (FBP) had been brought forward (Johns et al.: J. Clin. Invest. 1961; 40: 1684), Rothernberg et al., first found FBP in cells of human body (Proc. Soc. Expl. Biol. Med. 1970; 133: 428. J. Clin. Invest. 1971; 50: 717), and Lesli et al., also isolated FBP from cell membranes (Biochem. 1972; 11: 1969). Antony et al. systematically studied on placenta cells and definitely proposed that said FBP has a function as folic acid receptor (FR) on the cell membrane (J Biol Chem 1981; 256(18): 9684), and systematically and successively illustrated the biochemical properties of FR (Blood 1992; 79 (11): 2807, Annu. Rev. Nutr. 1996; 16: 501) FR is a kind of FBP anchored on glycerophosphatide inositol (GPI) in cell membranes, which can be cut from the cell membrane by GPI-specific phosphatidase C or D (Lee et al: Biochem. 1992: 31: 3236, Verria et a: J Biol. Chem. 1992; 267(6): 4119). FR is uniformly located on the surface of cell membrane essentially, and after binding with folic acid, it can be shifted into coated pits or coveolae, upon promoted by the initiator, and therefore be clustered (Mayor et al: Science 1994; 264: 1948), then folic acid is transferred into the cell by the resulted endocytosis (Anderson et al: Science 1992, There are mainly three forms of FR in human body: FR-α FR-β and FR-γ, wherein FR-γ is a kind of secreting protein expressed on hematopoietic cells (Shen et al: Biochem 1995; 34: 5660). FR-α and FR-β also exist in the surface of animal cell, wherein FR-α is mainly expressed on tumor cells and kidney cells, and FR-β is expressed on hepatic cells. Folic acid can adjust the affinity and density of cells to a certain extent. After limiting the taking dosage of folic acid, the affinity of FR-α to folic acid decreases, the density of FR-α increases in tumor cell and decreases in kidney cell, while that of FR-β is not obviously affected (Gates et al: Clin Cancer Res 1996; 2:1135).

With the disclosures that the expression number or activities of FR on most tumor cells are remarkably higher than that on normal cells (Cambell et al: Cancer Res 1991; 51: 5329. Coney et al: Cancer Res 1991; 51:6125. Weitman et al: Cancer Res 1992; 52:3396), the researches of using folic acid as guiding media to target tumor cells develop rapidly.

The results of animal experiments of tumor image diagnosis show that the complexs of folic acid as FR ligand directly or indirectly binding with radionuclides have remarkable target effect on tumor site (Low et al: WO96/36367 Nov. 21, 1996; U.S. Pat. No. 5,688,488 Nov. 18, 1997).

The cell culturing results of folic acid-PEG-liposome obtained by indirectly binding folic acid with surface of liposome show that the target effect to tumor cells of said folic acid-PEG-liposome is better than that of PEG-liposome or normal liposome (Lee et al: J Biol Chem 1994; 269(5), 3198. Wang et al: Proc Natl Acad Sci USA 1995; 92:3318. Lee et al: Biochim Biophys Acta 1995: 1233:134. Vogel et al: J Am Chem Soc 1996; 118(7): 1581. Thompson et al: WO97/31624 Sep. 4, 1997. Lu, Yaowei et al: Transaction of Shanghai University of Medical Science 2000; 27(1): 4).

The complexs of folic acid-polymer can transfer and release wholly said polymer into non-lysosome plasma of cells via FR. The bovine serum albumin, bovine immune albumin, horseradish peroxidase, ribonuclease, bean seninase inhibitor and anti-DNA oligonucleotide, which are bound with folic acid, can obviously be introduced into KB cells (human nasopharyngeal carcinoma cells), Hela cells (human cervical carcinoma cells) and XC cells (fibroblasts transfected with Rous sarcoma virus) to show their corresponding effects (Leamon et al Proc Natl Acad Sci USA 1991, 88:5572. Low et al: WO90/12096 Oct. 18, 1990). The anti-T cell receptor monoclonal antibody or anti-Fc receptor monoclonal antibody, which are bound with folio acid, can closely bind tumor cell, T-cell or natural killer cell, monocytes and macrophages together to fulfill the purpose of resolving said tumor cell (David et al: WO96/34630 Nov. 7, 1996). Moreover, after bound with folic acid, the toxins (Momordin, a kind of protein toxin its cytotoxicity can be shown only after passing through ribosome and entering into cell plasma, exotoxin fragments of pseudomonad (LysPE38 and CysPE35)) having function of inhibiting synthesis of protein show greatly improved abilities to suppress the growth of tumor cells (Leamon et al: j Biol Chem 1992; 267(35); 249666. 1993: 268(33): 24847).

Dextran (dextran) is a polymer of D-glucose obtained by fermenting saccharose with leuconastoc mesenteroidas (Gronwall et al: Acta Physiol Scand 1994; 7:97. 1945; 9:1. U.S. Pat. No. 2,437,518. U.S. Pat. No. 2,644,815). The linking manners of glucosyls in Dextran are different between each other of different Dextranes obtained with different strains, but the main linking manner is α-1,6 bond, and the others are α-1,4 bond or α-1,3 bond (Van Cleve et al: J Am Chem Soc 1956; 78:4435. Xu, Danfeng et al: Transaction of Pharmacology 1986; 21(3), 204). The animal experiments and tracing results of clinic experiments show that, after injecting Dextran, no abnormity and tissue damage is found in substantive organs of animals (Boyd et al: Lancet 1953; 1: 59. Gronwall et al: Acta Physiol Scand 1945; 9: 1), and no accumulation of Dextran exist in liver, spleen, kidney, lung and other organs of human body (Wilkinson et al: J Interal chir 1951; 11: 186). Clinically, Dextran is mainly used as blood volume enlarging agent (Gelin et al: Acta Chir Scand 1961; 122: 309) and blood fluidity improving agent (Gelin: Sock Pathogenesis and Therapy 1962; P332) to treat hemorrhagic shock, burn and liver-kidney syndrome, acute thrombus, thrombotic occlusive angiitis, cardiac infarction, generalized sclerosis and etc.

Because Dextran has specific biologic feature of having multiple hydroxyl groups, it has been used as carrier for many medicaments to fulfill the purposes of strengthening chemical stability of said medicaments or improving biologic availability of said medicaments or diagnosing diseases of lymphatic system. These Dextran-medicament complexs includes: Dextran-antimony (Mikhail et al: Exptl Parasitol 1975; 37: 348), Dextran-iron (Beresford et al: Brit J Pharmacol 1957; 12: 107), Dextran-insulin (Armstrong et al: Biochim Biophys Res Comm 1972; 47: 354), Dextran-daunomycin (Bernsten et al: J Nalt Cancer Inst 1978; 60(2): 379), Dextran-mitomycin C (Kojima et al: J Pharmacol 1980; 32:30), Dextran-Vitamin $B_{12}$ (Scrollini en al Eur J Med Chem 1974; 9: 621), Dextran-amethopterin (Hubert et al: EP0383170A2), Dextran-α (or β)-diastase (or trypsase) (Marshall et al: Arch Biochem Biophys 1975; 167:777), Dextran-sulfate (Kozo Yamada et al: Jap Circul j 1961; 25: 570, 575, 579), radioactive technetium ($^{99m}$Tc)-Dextran (Henze et al: J Nucl Med 1982; 23: 923. Ercan et al: Eur J Nucl Med 1985: 11: 80. Lu, Weiyao et al: Transaction of Shanghai University of Medical Science 1991; 18(4): 246. Liu, Yongchang et al: China J Nucl Med 1993; 13(3): 143). Among above Dextran-medicament complexs, the $^{99m}$Tc-Dextran 105 injection and stannous-Dextran 105 injection, which are developed by the inventor and used for locating affected part of diseases of lymphatic system and for assistant diagnosis of lymphatic metastasis tumor, have been formally produced and clinically used.

In sum, the FR on the surface of tumor cell is an effective pathway to introduce medicaments of radionuclide, liposome and polymer into said tumor cell via folic acid; Dextran is studied for a long time used as blood volume enlarging agent and carrier of radionuclide and other medicament, but the Dextran per se shows no antineoplastic effect. So far, there is no document or patent to research complexs of folic acid and polysaccharides, especially the complexs of folic acid and Dextran, and their uses as antineoplastics.

SUMMARY OF THE INVENTION

The present invention relates to a folic acid-polysaccharide complex of formula X-Y, wherein X is selected from the group consisting of folic acid, derivatives thereof, and other substances that can enter into cell via the pathway of folic acid receptor on the cell membrane, and Y is polysaccharides.

More specifically, the present invention relates to a folic acid-polysaccharide complex of formula $(X)_n$—Y, wherein X is identical or different, and is selected from folic acid, derivatives of folic acid and other substances that can enter into cell via the pathway of folic acid receptor, Y is one of polysaccharides other than arabinogalactan; $n \geq 1$.

The present invention also relates to pharmaceutical compositions having said folic acid-polysaccharides complex and pharmaceutical adjuvants.

The present invention also directs to the use of said folic acid-polysaccharide complex in preparation of medicament for antineoplastics.

On the other hand, the present invention relates to a method for treating tumor in the folic acid receptor positive patient, which comprises administering effective amount of said folic-polysaccharide to the individual to be treated.

The present invention also relates to folic acid-polysaccharide complexes used as medicaments.

DETAILED DESCRIPTION OF THE INVENTION

The present invention provides a group of folic acid-polysaccharide complexes as defined above. Surprisingly, it is found that said complexes cannot only enter into cells via the pathway of folic acid receptor on the cell membranes, but also kill tumor cells in vivo and suppress the growth of tumor tissues without injuring normal cells.

The substance X of folic acid, derivatives of folic acid or other substances that can enter into cell via the pathway of folic acid receptor, which the present invention relates to, has no notable toxic and side effect on cells of animals or human body, and is selected from the group consisting of folic acid, folinic acid, dihydrofolic acid, tetrahydrofolic acid, tetrahydropterin, pteroylpolyglutamic acid, 2-deamino-hydroxy-folic acid, 1-denitro-folic acid, 3-denitro-folic acid, 8-denitro-folic acid and etc., wherein "denitro" means, that the nitrogen atom of said position of folic acid is replace with carbon atom. Preferably, X is folic acid, dihydrofolic acid or tetrahydrofolic acid, and more preferably is folic acid.

The different kinds of polysaccharide Y, which the present invention relates to, have no remarkably and directly suppressing activity to tumor cells of animals or human body and the growth thereof, and they do not possess ligand property of receptor. These polysaccharides comprise: (1) dextrans, such as: Dextran, nigeran, pullulan, scleroglycan, lentinan, krestin (coriolan polystictin), pachymaran (pachman), cordyceps polysaccharide (cordycepose), agaric polysaccharide, lentinan, schizophyllan, armilarielia tabescens polysaccharide, Hericium erinaceus polysaccharide (hedgehog fungus), tremellas, *Neurospora crassa* polysaccharide, coprinus polysaccharide, lichenan, heterolichenan, laminarin, xuchangqing polysaccharid, angelica polysaccharide, stephania tetrandra polysaccharide, astragalus polysaccharides, laminarin, amylose, dextrin and etc.; (2) polysaccharoses, such as: polysaccharose; (3) fructosan, such as siberian solamonseal rhizome polysaccharide, lycoris polysaccharide, barley polysaccharide and scilla maritime polysaccharide, levuloside of phlean and couch grass polysaccharide; (4) heteropolysaccharides, such as: cladospore polysaccharide, hetetopenicillic polysaccharide, absidia polysaccharide, Neurospora crassa polysaccharide, ganoderma polysacchatides, porphyran, manyprickle acanthopanax root polysaccharide, konjak polysaccharide, ginseng polysaccharide, indicalamus polysaccharide, bagasse polysaccharide, medlar polysaccharide, glossy privet fruit; polysaccharide, tabasheer polysaccharide, tea polysaccharide and etc., (5) mono- or heteropolysaccharide sulfates, such as: agar polysaccharide, carragheen polysaccharide, gingko algae polysaccharide, chlorella polysaccharide, fucoidin, heparin, chondroitin sulfate and etc.; (6) mono- or heteropolysaccharide aldonic acidic polysaccharides such as ginseng pectin polysaccharideand other pecitc polysaccharides, arabic gum, gummi tragacanthae, gumghatti, tragacanth, alginate and etc.; and (7) other hydrophilic polymers, such as: polyethylene Oxide, methoxypolyethylene glycol etc.

In the present invention, the preferably selected polysaccharides are those having molecular weight of 4,000 to 2,000,000.

In a preferable embodiment, the polysaccharide Y is Dextran, and the preferable molecular weight of said Dextran is 10,000 to 2,000,000, more preferably is 10,000 to 150,000, and most preferably is about 105,000.

In foregoing formula of $(X)_n$—Y, n is a integer greater than or equal to 1. The upper limit of n is not important, and is defined based on the type and molecular of the polysaccharide to be used. The value of n can be adjusted by controlling the ratio of raw materials in the condensation reaction for producing said folic acid-polysaccharide complex. A technician in the art can select the optimal value of n for a certain folic acid-polysaccharide complex by conventional methods, such as by determining the antineoplastic activity of said complex.

When n is greater than 1 in above formula, X can be identical or different. In the present invention, the preferable X is identical.

In the present invention, the term of "folic acid-polysaccharide complex" means the free complex and its appropriate medicinable salts. When alkali nitrogen atom exists in molecule of said complex, it can form salts with medicinable inorganic acids or organic acids, such as: hydrochloric acid, sulfuric acid, phosphoric acid, acetic acid, propionic acid, succinic acid, maleic acid, dihydroxy-naphthoic acid, methylsulfonic acid, glycollic acid, benzene sulfonic acid, p-toluene sulfonic acid, naphthalene sulfonic acid and etc. When free carboxyl groups exist in molecule of said complex, it can form salts with medicinable inorganic bases or organic bases, such as: sodium hydroxide, potassium hydroxide, ammonium hydroxide, triethylamine, ethanolamine, dimethylamino-pyridine and etc.

In the folic acid-polysaccharide complex of the present invention, the folic acid (X) and polysaccharide are linked with covalent bond, preferably With ester bond formed between carboxyl of folic acid and hydroxyl of polysaccharide. The coupling between said folic acid and polysaccharide is carried out by known methods. For example, the carboxyl of said folic acid is first activated with dehydrating agents, such as: hydroxy-diimidazole, carbodiimide and etc., which are disclosed in WO90/12096 and WO96/34630, and then reacted with hydroxyl of polysaccharide to form ester bond to obtain the complex of the present invention.

In a preferable solution for producing said complex, folic acid and polysaccharide condense in the presence of alkali catalyst and dehydrating agent, in which the alkali catalyst can be triethylamine, pyridine and etc, preferably be pyridine and dimethlyamino-pyridine, and the dehydrating agent is preferably carbodiimide type dehydrating agent, such as dicyclohexyl-carbodiimide and 1-ethyl-3-(3-dimethylamino-propyl)-carbodiimide. The reaction is carried out preferably in inert organic solvent, such as aromatic hydrocarbon (benzene, toluene and etc.), ketone (acetone), halohydrocarbon (dichloromethane, trichloromethane and etc.), acid amide (formamide, N,N-dimethyl-formamide), sulfoxide (dimethylsulfoxide) and their arbitrary mixtures, more preferably in non-proton polar solvent, such as N,N-dimethyl-formamide, dimethylsulfoxide and their mixtures with other solvents.

The above condensation reaction normally is carried out at temperature from the room temperature to refluxing temperature of mixture of reaction, and preferably at moderate temperature such as room temperature.

The reaction time is generally from several minutes to several dozens of hours, preferably from 10 minutes to 24 hours, and more preferably from 20 minutes to 20 hours.

After ending the reaction, the complex of the present invention can be isolated and purified from the reaction mixture by conventional methods, such as filtrate, deposition, crystallization, dialysis, silicic acid chromatography, exclusion chromatography and etc., preferably purified by dextran gel exclusion chromatography such as using Sephadex G-15 and Sephadex G-25 columns and etc.

The following experiment is used to estimate the folic acid-polysaccharide complex of the present invention.

1. Demonstration of that said folio acid-polysaccharide complex enters into tumor cell via folic acid receptor pathway. The folic acid-Dextran labeled with fluorescein and is used as a model medicament, and the tumor cells are cultured in vitro. Whether the folio acid-Dextran ingested by the tumor cells has an obvious saturated trend, and whether the extent of intake of folic acid-Dextran is higher than that of Dextran are learned by testing the change of ingested folic acid-Dextran by the tumor cells at different culturing concentration and the difference between it and that of ingested pure Dextran, and the change of intake of folic acid-Dextran at the same culturing concentration and different culturing time; whether the free folic acid can obviously and competitively inhibit the intake of folic acid-Dextran is learned by testing the change of ingested folic acid-Dextran by the tumor cells at the same culturing concentration and time and different concentration of free folic acid; whether the decrease of folic acid receptor on the tumor cell membrane can affect the quantity of folic acid-Dextran ingested by said tumor cells is learned by testing the quantity of folic acid-Dextran ingested by the tumor cells that are pre-treated with phosphatidase D having different concentrations. Finally, whether said folic acid-Dextran can enter into the tumor cell via the folic acid receptor pathway is comprehensively estimated.

2. Observation of the intake of folic acid-polysaccharide by tumor cells in vivo. The folic acid-Dextran or Dextran, which are labeled with fluorescein, is injected beside the tumor on the naked mice having tumor, then the naked mice is killed after 24 hours, and the fluorescence intensity and distribution in tumor cell of the tumor tissue are observed to learn the effect of selective intake of folic acid-polysaccharide in tumor cell in vivo.

3. Effect of folic acid-polysaccharide in suppressing tumor in vivo. The naked mice having tumors are divided into blank group, Dextran group and folic acid-Dextran group, and then they are injected or not injected with folic acid-Dextran or Dextran beside the tumors respectively. The change of size and weight of tumors, the change of morphology and structure of tissue of tumors and the change of DNA ploid in tumor cells after administering small and high doses in sequences are observed to learn the effect of folic acid-polysaccharide in suppressing tumor in vivo of naked mice having tumor.

4. Estimation of the safety of folic acid-polysaccharide. The biggest defect of chemotherapeutics of tumor lies in their greater toxicity and side effect. Whether said folic acid-polysaccharide has the same defect is studied by acute toxicity test of folic acid-polysaccharide. The activity level, the change of weight and the death of mice, and the damage of main visceral organs of killed mice are observed after intravenous injection of the folic acid-Dextran with maximum concentration to elementarily learn the safety of folic acid-polysaccharide as an antineoplastic.

In the present invention, aforementioned dextran, polysaccharose, mono- or heteropolysaccharide sulfate and mono- or heteropolysaccharide aldonic acidic polysaccharide, which have molecular weight of 4,000–2,000,000, are reacted with folic acid to obtain folic acid-polysaccharide complex having linkage of covalent bond. By selecting folic acid-Dextran complex as model medicament, wherein the molecular weight of Dextran is 105,000, the results of aforementioned experiments are as follow.

1. To culture tumor cell in vitro. The results of culturing Hela229 in vitro of folic acid-Dextran show: (1) the intake of folic acid-Dextran increases with the increase of culturing concentration, but the increase extent gradually slows down (see FIG. 1), and the intake of folic acid-Dextran is 2.7 times higher than that of Dextran when the concentration of folic acid-Dextran is 4.5 mg/ml; (2) the intake of folic acid-Dextran increases with the extension of culturing time, but the increase extent gradually slows down (see FIG. 2); (3) the intake of folic acid-Dextran decreases remarkably with the increase of concentration of folic acid in culture fluid (see FIG. 3); (4) the intake of folic acid-Dextran decreases obviously with the concentration of phosphatidase D) used to pre-treat HeLa229 cells (see FIG. 4). It can be seen that folic acid-Dextran can enter into HeLa229 cell via folic acid receptor pathway, and the intake thereof is remarkably higher than that of Dextran.

2. The experiments of tumor cell targeting and tumor suppressing in vivo of naked mice having tumor. The results of the tumor cell targeting experiment carried out by injecting folic acid-Dextran beside the tumor of the naked mice having tumor, which is inoculated with HeLa229 cells, show that the quantity of folic acid-Dextran, which enters into the tumor cell after it diffuses in the tumor tissue, is obviously higher than that of Dextran (see FIG. 5), and the tumor target in vivo is apparent. The results of the tumor suppressing experiment using folic acid-Dextran to the naked chmice having tumor, which is nacukated with HeLa229 cells, show: (1) the growth of the tumor is slowed down at small dose of folic acid-Dextran: and the growth of the tumor is suppressed at high dose of folic acid-Dextran (see FIG. 6); (2) after administering for 33 days, the tumors of killed mice of folic acid-Dextran group are obviously smaller than that of blank group and Dextran group (see FIGS. 7 and 8), and the suppression ratio of tumor is about 75%; (3) folic acid-Dextran has an obvious effect to destroy the tumor tissue as compared with blank group and Dextran group (see FIGS. 9a, 9b and 9c); (4) folic acid-Dextran can remarkably bring down the DNA index (i.e. the ratio of DNA mass in tumor cells to DNA mass in normal cells, and it is represented with DI hereinafter) in tumor cells of tumor tissue, wherein the DI is 3.5 in blank group, 3.1 in Dextran group and 2.3 in folic acid-Dextran group.

3. Acute toxicity test. The results of acute toxicity test show that the activities of mice are normal, the weight of mice increase, and no mice is dead, and no notable abnormity in main visceral organs is observed, after intravenously injecting 1.5 g/kg folic acid-Dextran (because the lower solubility, it is the maximum concentration to carry out the experiment for testing the maximum tolerance dose) into male and female mice respectively and observing 7 days.

The above results of experiments prove that the present invention has following merits: (1) Dextran per se has no antineoplastic effect; (2) folic acid Dextran can enter into cell via folic acid receptor pathway, and has obvious effect to suppress the growth of tumor tissue, high safety and lower toxicity and side-effect; (3) the antineoplastic effect of said folic acid-Dextran is different from that of conventional chemotherapeutics, so the present invention provides a new method to treat tumor with medicament.

Based on the aforementioned experiments of folic acid-polysaccharide, the present invention can combine with pharmaceutical acceptable excipient, adhesive, suspending agent, disintegrant, dilutent, lubricant, enteric coating materials, biologic adhesion materials, non-water-soluble framework materials and other adjuvants with said folic acid-polysaccharide to prepare corresponding pharmaceutical compositions. The different dosage form of pharmaceutical composition of the present invention can be produced by the conventional methods in pharmacological field.

The preferable pharmaceutical compositions comprise: folic acid-polysaccharide solution or freeze drying product that can be mixed with water for injection to prepare solution in-site for intravenous injection or for injecting in or beside tumor; peroral dry syrup of folic acid-polysaccharide having sodium hydrogen carbonate or aluminum hydroxide and magnesium trisilicate; and peroral enteric capsule of folic acid-polysaccharide. Said compositions can also be peroral enteric tablet of folio acid-polysaccharide, microbead of folic acid-polysaccharide used for artery embolism, peroral parvule of folic acid-polysaccharide used for colon releasing, or biologic adhesion microbead of folic acid-polysaccharide used for spraying in nasal cavity, uterine cavity and other cavities or injecting in abdominal cavity.

DETAILED DESCRIPTION OF THE SPECIFIC EMBODIMENTS

Figure 1:
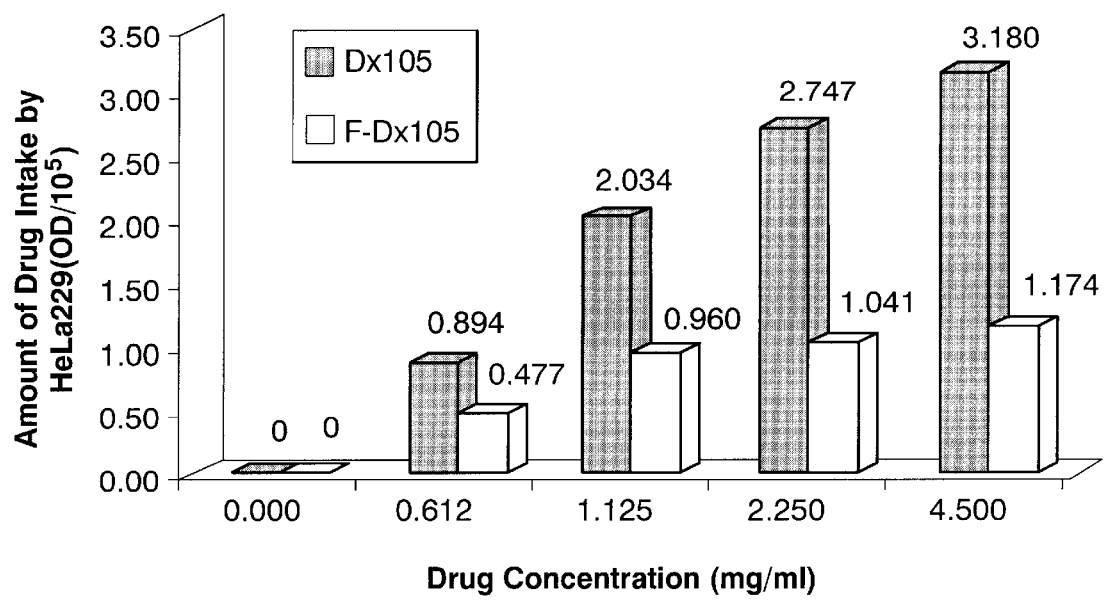
FIG. 1 shows: the intakes of F-Dx105 and Dx105 (culturing at 37° C. for 4 hours) by Hela229 cells at different culturing concentrations.

The following non-restrictive embodiments are used to further detailedly describe the present invention.

EXAMPLE 1

Preparation of Folic Acid-Polysaccharide (F-PS)
1. Preparation of FOPS
   (1) Folic Acid-Intradex (F-Dx)
   Effect of Molecular Weight of Dx 0.74 g Dimethylamino-pyridine is dissolved in 12 ml mixture solvent of formamide/N,N-dimethylformamide/dichloromethane (10:9:1), then adding 0.25 g F and 1.16 g dicyclohexyl-carbodiimide, adding 6 ml Dx solution (molecular weight: 10,000) dissolved in said mixture solvent (0.1 g/ml), reacting at 25° C. for 20 hours in dark, filtering after ceasing the reaction, pouring the filtrate into acetone to form a light yellow deposit, filtering and collecting said deposit, drying at vacuole to obtain crude F-Dx product, purifying with Sephadex G-15 column and eluting with redistilled water, collecting the first chromatographic section of eluting liquid and freeze drying to obtain pure F-Dx product.

Dx (molecular weight: 70,000) is reacted with F and treated as above mentioned methods.
   Dx (molecular weight: 105,000) is reacted with F and treated as above mentioned methods.
   Dx (molecular weight: 500,000) is reacted with F and treated as above mentioned methods.
   Dx (molecular weight: 2,000,000) is reacted with F and treated as above mentioned methods.

The Effect of Mass Ratio of F and Dx
   The reaction mass ratio of Dx (molecular weight: 105,000) and F is 2.4:1 (g/g), and the reaction and treatment as above mentioned are carried out.
   The reaction mass ratio of Dx (molecular weight: 105,000) and F is 1.71:1 (g/g), and the reaction and treatment as above mentioned are carried out.
   The reaction mass ratio of Dx (molecular weight 105,000) and F is 1.33:1 (g/g), and the reaction and treatment as above mentioned are carried out.
   The reaction mass ratio of Dx (molecular weight: 105,000) and F is 1.20:1 (g/g), and the reaction and treatment as above mentioned are carried out.

(2) Folic Acid-Polysaccharose (F-Ficoll)
   0.6 g Ficoll (molecular weight of 400,000) is used to replace 0.6 g Dx (molecular weight of 10,000), and the reaction mass ratio Of Ficoll and F is 2.4:1 (g/g), then the same reaction and treatment as used to prepare F-Dx are carried out.

(3) Folic Acid-Dextrin (F-Dextrin)
   0.74 g Dimethylamino-pyridine is dissolved in 8 ml dimethylsulfoxide, then adding 0.25 g F and 1.16 g dicyclohexyl-carbodiimide, adding 4 ml Dextrin solution (molecular weight: 4,500) dissolved in dimethylsulfoxide (0.15 g/ml), and in sequence reacting and purifying by the same methods as used to prepare F-Dx.

(4) Folic Acid-Heparin (F-Heparin)
   0.37 g Dimethylamino-pyridine, 0.125 g F and 0.58 g dicyclohexyl-carbodiimide are dissolved in 6 ml mixture solvent of formamide/N,N-dimelylformamide/dichloromethane (10:9.1), then adding 10 ml Heparin sodium solution (molecular weight: 2,000–6,000) dissolved in said mixture solvent (0.03 g/ml), subsequently reacting by the same method as used to prepare F-Dx, and purifying by the same method, except the eluting liquid is a mixture liquid of 5 mM sodium hydrogen carbonate and 0.1M sodium chloride.

(5) Folic Acid-Acacia (F-Acacia)
   0.6 g Acacia (molecular weight of 240,000–580,000) is used to replace 0.6 g Dx (molecular weight of 10,000), and the reaction mass ratio of Acacia and F is 2.4:1 (g/g), then the same methods of reaction and purification that are used to prepare F-Dx, except the filtrate is poured into ethanol, are carried out.

(6) Dihydrofolic Acid-Dextran ($F_2$-Dx)
   0.74 g Dimethylamino-pyridine is dissolved in 12 ml mixture solvent of formamide/N,N-dimetylformamide/dichloromethane (10:91), then adding 0.25 g $F_2$ and 1.16 g dicyclohexyl-carbodiimide, adding 6 ml Dx solution (molecular weight: 105,000) dissolved in said mixture solvent (0.1 g/ml), and subsequently reacting and purifying by the same method as used to prepare F-Dx (7) Tetrahydrofolic Acid-Dextran ($F_4$-Dx)
   0.74 g Dimethylamino-pyridine is dissolved in 12 ml mixture solvent of formamide/N,N-dimetylformamide/dichloromethane (10:9:1), then adding 0.25 g $F_4$ and 1.16 g dicyclohexyl-carbodiimide, adding 6 ml Dx solution (molecular weight: 105,000) dissolved in said mixture solvent (0.1 g/ml), and subsequently reacting and purifying by the same method as used to prepare F-Dx.

2. Analyzing F-PS
   By using high performance silica gel plate as carrier and trichloromethane/methanol/acetic acid as development system, and ascendingly developing and drying and coloring with iodine vapor, the point of free folic acid in the sample is not found. F-PS and F samples has exactly the same characterizing absorption peaks at 258, 285 and 365 nm, and the same ratio of A258/A365 of 2.9–3.1, after independently scanning 0.4% sodium hydroxide solution samples of F-PS and F within the same wavelength as above used. Using F as standard, the binding ratio of F in said F-PS sample determined at 365 nm is as follows.

| Binding ratio of F in F-PS having Dx with different molecular weight (Raw materials ratio of Dx/F = 2.4/1 (W/W)) | | | | | |
|---|---|---|---|---|---|
| Molecular weight of Dx | 10,000 (Dx10) | 70,000 (Dx70) | 105,000 (Dx105) | 500,000 (Dx500) | 2000,000 (Dx2000) |
| Binding ratio of F (W/W) | 8.51% | 6.38% | 8.98% | 8.54% | 8.41% |
| Molar ratio (F/Dx) | 2:1 | 11:1 | 23:1 | 105:1 | 416.1 |

| Effect of ratio of raw materials of Dx/F on the binding ratio of F (Dx105) | | | | |
|---|---|---|---|---|
| Dx/F (W/W) | 2.4:1 | 1.71:1 | 1.33:1 | 1.20:1 |
| Binding ratio of F (W/W) | 10 ± 1% | 16 ± 1% | 23 ± 1% | 25 ± 1% |
| Molar ratio (F/Dx) | 26:1 | 45:1 | 71:1 | 80:1 |

When raw materials ratio of Ficoll-400 (molecular weight of 400,000)/F is 2.4:1 (W/N), the binding ratio of F is 12.04% (molar ratio of F/Ficoll=109.1).

When raw materials ratio of Dextrin-4.5 (molecular weight of 45,000)/F is 2.4:1 (W/N), the binding ratio of F is 18.38% (molar ratio of F/Dextrin=1.87:1).

When raw materials ratio of Heparin (molecular weight of 2,000–6,000)/F is 2.4:1 (W/N), the binding ratio of F is 7.86% (molar ratio of F/Heparin=039–1.16:1), When raw materials ratio of Acacia (molecular weight of 240.000–580,000)/F is 2.4:1 (W/W), the binding ratio of F is 4.53% (molar ratio of F/Acacia=1.87:1).

EXAMPLE 2

Preparation of Folic Acid-Dextran-Fluorescein Isothiocyanate (F-Dx105-FITC)

1. Preparation of Dextran-Fluorescein Isothiocyanate (Dx105-FITC)

(1) The preparation of ferric acetylacetone (FAA) comprises: dissolving 1.84 g sodium acetate and 2 g ferric trichloride in 6 ml distilled water, adding 12 ml acetylacetone, filtering and drying at vacuum to obtain crude FAA product, dissolving said crude product in distilled water, extracting with ethyl ether for three times, merging all extract liquids, and removing ethyl ether by vacuum distillation, recrystallizing with 60% methanol to obtain red-brown FAA crystal with m.p. of 183–184° C.

(2) The preparation of Dx105-FITC comprises: dissolving 0.2 g Dx105, 20 mgFITC and 20 mgFAA in 2 m] dimethylsulfoxide, reacting at 95° C. for 2 h in dark, filtering, vacuum drying at 80–90° C. for 2 h to obtain Dx105-FITC crude product, purifying by Sephadex G-15 column chromatography, freeze drying to obtain Dx105-FITC pure product.

(3) The analysis of Dx105FITC comprises: using high performance silica gel as carrier and trichloromethane:methanol:ammonia (6/3.5/0.5) as development system, ascendingly developing and drying, observing at 254 nm light and finding no free FITC spot in sample; scanning 0.4% sodium hydroxide solution samples of Dx105-FITC and TITC in the wavelength range of 230–550 nm, and finding that the samples of Dx105-FITC and FITC have exactly the same characterizing absorption peak at 492 nm; using FITC as standard, determining at 492 nm, and finding that the FITC binding ratio in Dx105-FITC sample is 3.6% (w/w).

2. Preparation of Folic Acid-Dextran-Fluorescein Isothiocyanate (F-Dx105-FITC)

(1) The preparation of F-Dx-FITC comprises: controlling raw materials mass ratio of Dx105-FITC and F at 2.4:1, preparing by using the same method as used to prepare F-Dx in example 1, and purifying with Sephadex G-15 column chromatography, and freeze drying to obtain F-Dx105-FITC pure product.

(2) The analysis of F-Dx105-FITC comprises: using the same analyzing method as used to analyze F-PS in example 1 to qualitatively determine free F in F-Dx105-FITC and quantitatively determine the binding ratio of F, and finding that the F binding ratio is 7.43% (w/w)

EXAMPLE 3

Selective Intake of F-Dx105 by HeLa229 Cells Via F Receptor in vitro

The HeLa229 cells (a kind of human cervical cancer cells, supplied by Shanghai Cell Institute of Chinese Academy of Sciences) are adherently pre-cultured at hexapore culture plate with 10% calf serum (NCS)/RPMI-1640 culture liquid at 37° C. in $CO_2$ incubator for 24 hours. Each pore (φ33 mm) contains $2\times10^5$ HeLa cells. The original culture liquid is removed before using.

1. Effect of Concentration of Sample on Intake

The F-Dx105-FITC solutions (0.612, 1.125, 2.25 and 4.50 mg/ml) and Dx105-FITC solutions (0.585, 1.17, 2.34 and 4.68 mg/ml), prepared with 1 ml RPMI-1640 culture liquid respectively, are added into pores having pre-cultured HeLa229 cells, then culturing at 37° C. in $CO_2$ incubator for 4 hours. Each pore is washed with 2 ml phosphate buffer liquid for 4 times, then rupturing cells with 1.5 ml 1% Triton X-100 phosphoric acid buffer liquid (pH 7.4). The optical density of fluorescence of cytolytic liquid having ruptured cells (OD) is determined by fluorospectropbotometer at 492 nm/512 nm. The results show that the intake of F-Dx105-FITC by HeLa229 cell increases obviously with the increase of the concentration of F-Dx105-FITC, while the increase extent gradually slows down, anyway it is higher that that of Dx105-FITC (see FIG. 1).

2. Effect of Culturing Time on Intake

Figure 2:
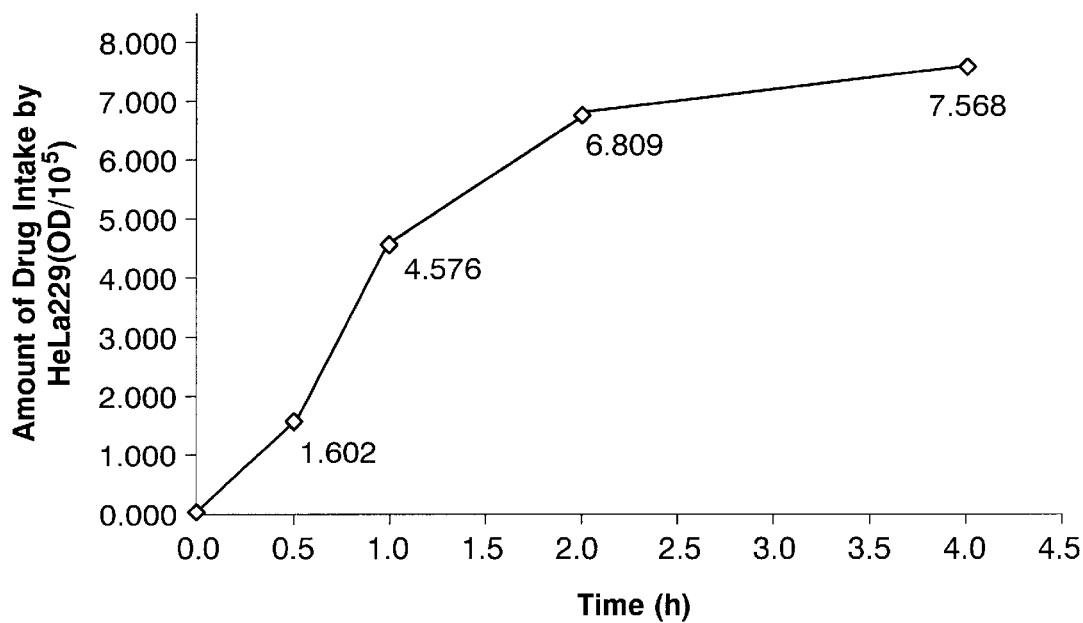
FIG. 2 shows: the intakes of F-Dx105 (culturing at 37° C., the culturing concentration is 4.5 mg/ml) by hela229 cells for different culturing time.

The solution of 4.50 mg/ml F-Dx105-FITC prepared with 1 ml RPMI-1640 culture liquid is added into pores having pre-cultured HeLa229 cells, then culturing at 37° C. in $CO_2$ incubator for 0.5, 1, 2 and 4 hours respectively, treating and determining optical density of fluorescence (OD) by the same methods as described above. The results showed that the intake of F-Dx105-FITC by HeLa229 cell increases obviously with the increase of the culturing time, while the increase extent gradually slows down (see FIG. 2).

3 Effect of Free Folic Acid on Intake

Figure 3:
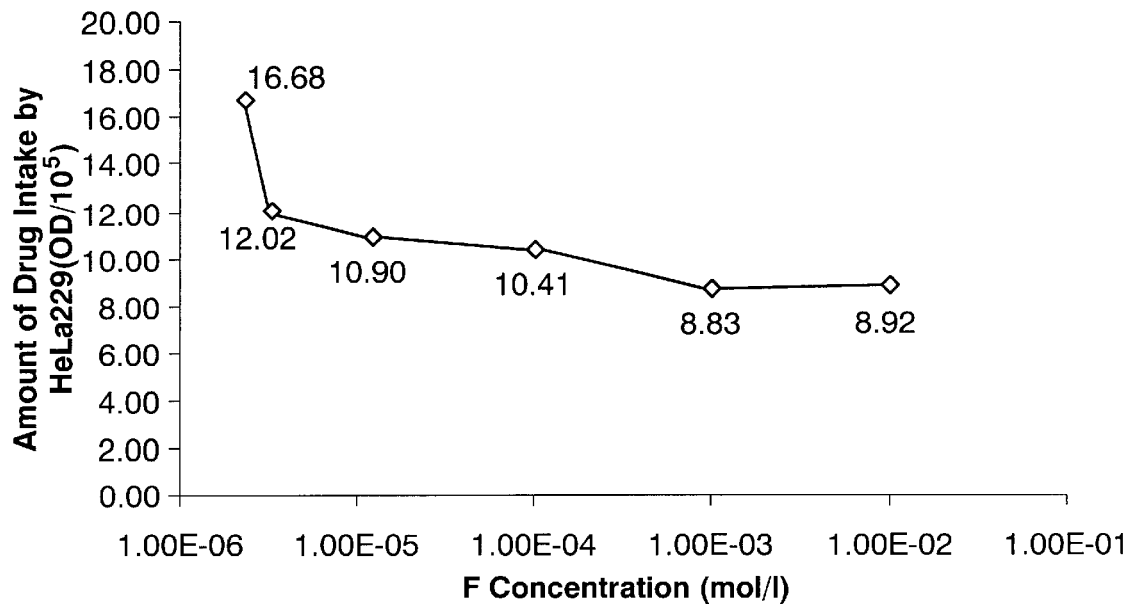
FIG. 3 shows: the intakes of F-Dx105 (culturing at 37° C. for 4 hours, the culturing concentration is 4.5 mg/ml) by hela229 cells at different concentrations of folic acid (F-concentration).
Figure 4:
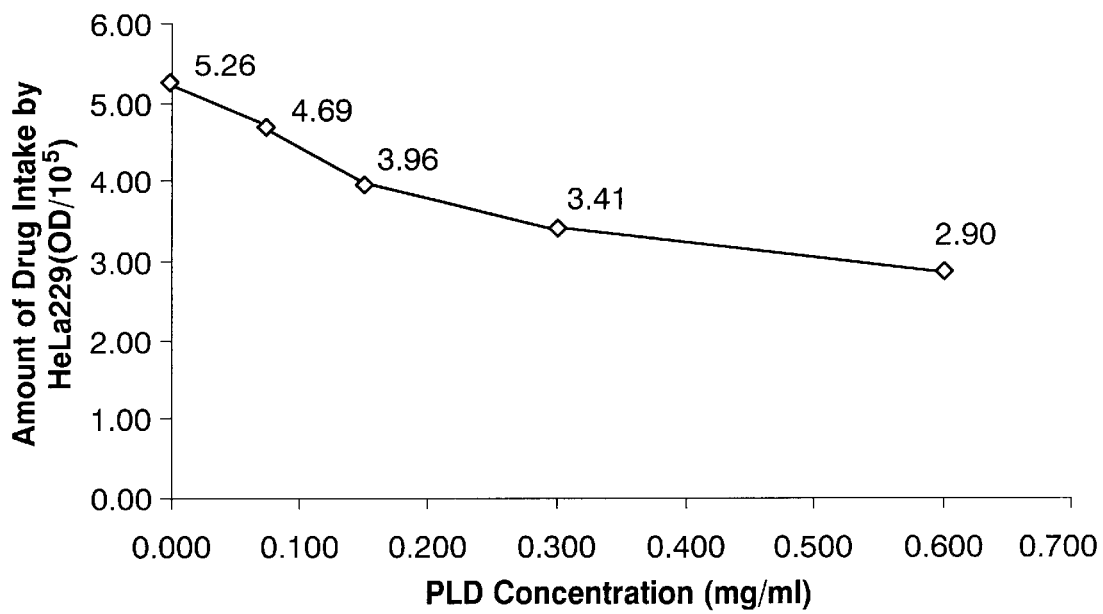
FIG. 4 shows: the intakes of F-Dx105 (culturing at 37° C. for 4 hours, the culturing concentration is 4.5 mg/ml) by hela229 cells that are pre-treated with phosphatidase D having different concentrations.

The solutions of 4.50 mg/ml F-Dx105-FITC having free F ($2.3\times10^{-6}$, $3.3\times10^{-5}$, $2\times10^{-5}$, $1.0\times10^{-4}$, $1.0\times10^{-3}$, $1.0\times10^{-2}$ mol), which are prepared with 1 ml RPMI-1640 culture liquid, are added into pores having pre-cultured HeLa229 cells, then culturing at 37° C. in $CO_2$ incubator for 4 hours, treating and determining optical density of fluorescence (OD) by the same methods as described above. The results showed that the intake of F-Dx105-FITC by HeLa229 cell decreases obviously with the increase of the concentration of free F (see FIG. 3).

4. Effect of Treatment of Enzyme on Intake

The pre-cultured HeLa229 cells are treated with RPMI-L 640 culture liquids respectively having 0, 0.075, 0.15, 0.30 and 0.60 mg/ml of phosphatidase-D (PLD, obtained from cabbage), then removing said culture liquids and washing with 1 ml RPMI-1640 culture liquid twice respectively, then adding solutions of 4.50 mg/ml F-Dx105-FITC prepared with 1 ml RPMI-1640 culture liquid into pores having above treated HeLa229 cells, culturing at 37° C. in $CO_2$ incubator for 4 hours, treating and determining optical density of fluorescence (OD) by the same methods as described above. The results showed that the intake of F-Dx105-FITC by HeLa229 cell decreases obviously with the increase of the concentration of PLD in treatment liquid (see FIG. 3).

EXAMPLE 4

Selective Intake of F-Dx105 by Hela229 in vivo

1. Building Naked Chmice Model Having HeLa229 Tumor

BALB/C naked chmices (18±1 g; female; provided by Tumor Institute of Shanghai City) are inoculated subcutaneously with 0.1 ml ($1\times10^7$) HeLa cells (provided by Shanghai Cell Institute of Chinese Academy of Sciences) at right forefoots near axilla, then they are fed in SPF barrier system to grow the larger tumor lumps via continuous reproduction of Hela cells in vivo, and killed to obtain tumor lumps with diameter of about 2 mm under aseptic condition. The said tumor lumps are transplanted at the same position of other naked chmices with the same specification via 20# trocar, then these chmices are fed for 10 days for following uses.

2. Intake of F-Dx105 by HeLa229 in vivo

Figure 5:
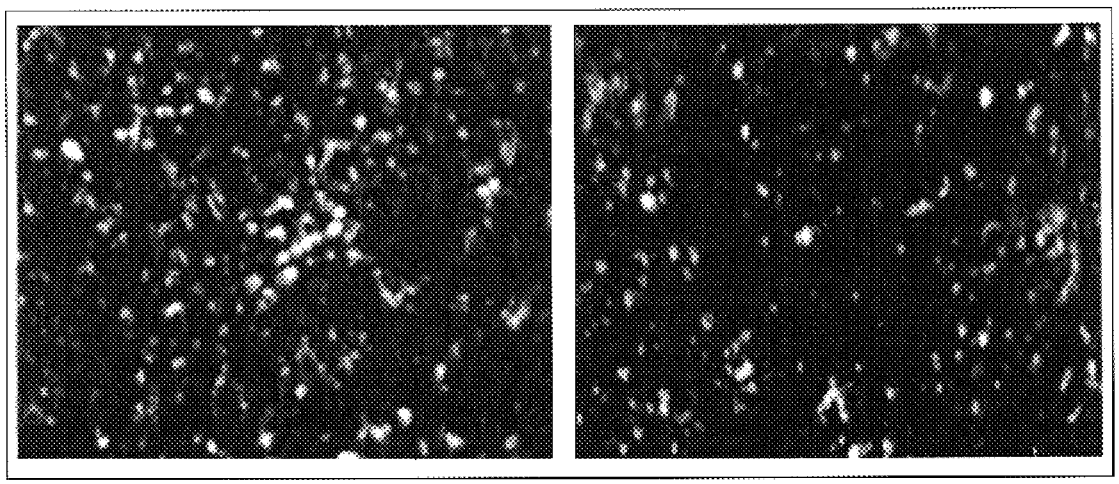
FIG. 5 shows: the fluorescence photos of tumor tissue slice (circular bright spots are fluorescence in the tumor cells), after 24 hours of injecting F-Dx105-FITC (left) or Dx105-FITC (right) beside the tumor of naked chmices having tumor, which are inoculated with HeLa229 cells.

Two groups of naked chmices having HeLa229 tumors (each group has 3 chmices) are subcutaneously injected with 0.1 ml F-Dx105-FITC (5.7 mg) and Dx105-FITC (5.7 mg)

beside tumors respectively, then they are fed for 24 h and killed. The tumor tissue slices obtained are contrastively observed and filmed by fluorescence microscope and phase contrast microscope. The results show that F-Dx105-FITC can obviously enter into HeLa229 cells after diffused in tumor tissue (see FIG. 5).

EXAMPLE 5

Tumor Suppression Effect of F-Dx105

In three groups of naked chmices having HeLa229 tumors (each group has 6 chmices), two, groups are subcutaneously injected with 0.1 ml F-Dx105 (1.12 mg) and Dx105 (1.12 mg) beside tumors respectively everyday for 6 days, and then they are subcutaneously injected with 0.3 ml Fr-Dx105 (10.52 mg) and Dx105 (10.52 mg) on the $20^{th}$ day. The chmices of residual group are used as bland group and not administered any medicament. All chmices of these three groups are fed for 33 days.

1. Dynamic Change of Tumor

Figure 6:
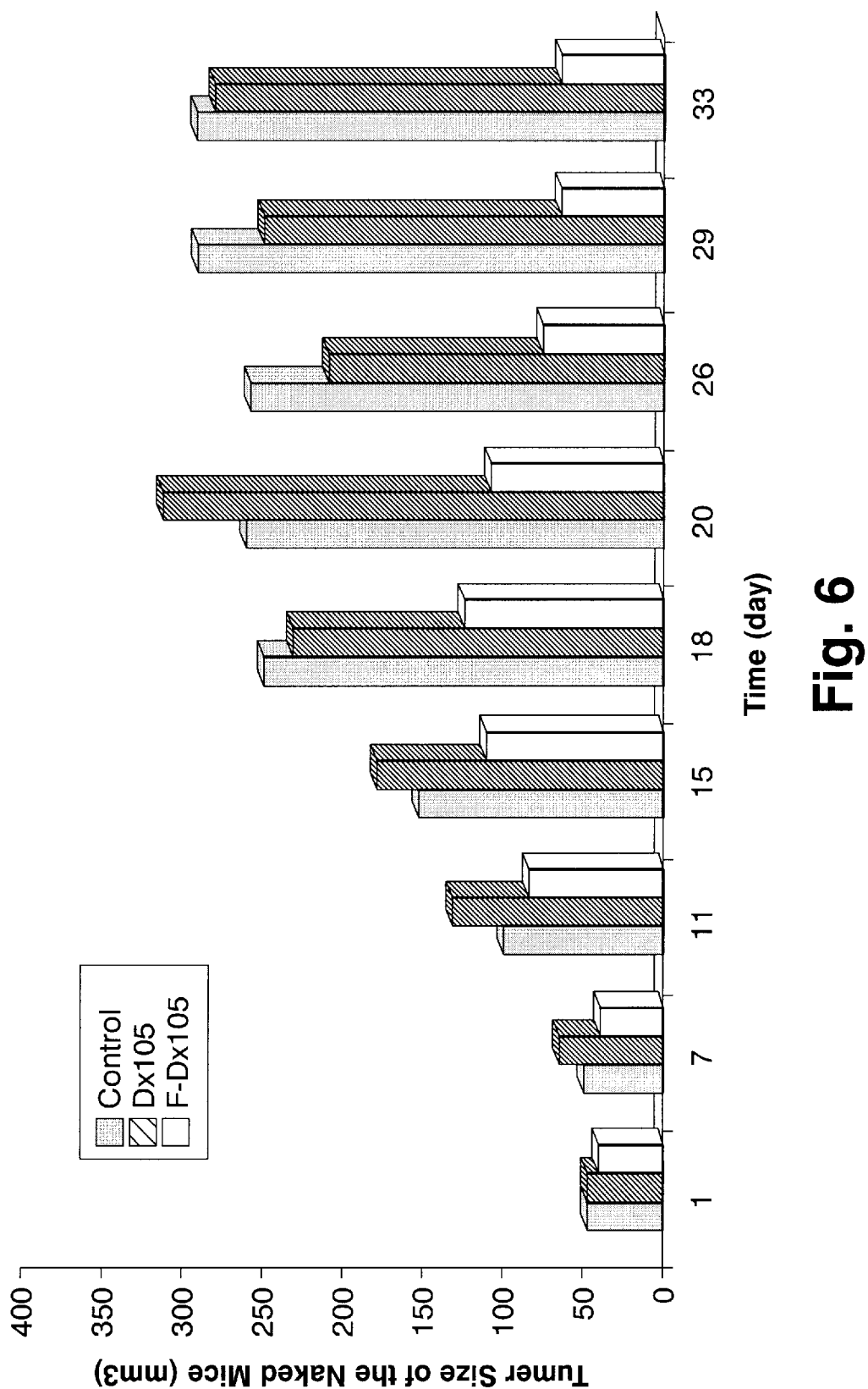
FIG. 6 shows: the dynamic change of tumor size ($V=\pi ab^2/6$) after injecting F-Dx105 and Dx105 respectively (in first to sixth days: 56 mg/kg, in $19^{th}$ day: 526 mg/kg) beside the tumor of naked chmices having tumor, which are inoculated with HeLa229 cells (6 chmices per group).

The sizes of tumor of said naked chmices having HeLa229 tumors of the three groups are determined every other day after administering, i.e. the size of tumor is calculated by experiential formula $V=\pi ab^2/6$, wherein (a) is longitudinal diameter, (b) is the maximum transverse diameter, and they all measured by caliper. The results show that the growth of tumors of F-Dx105 group is obviously slower than those of Dx105 group and bland group, and the growth of tumors of F-Dx105 group is obviously suppressed after administering complementary medicament with higher concentration, and the relapse of tumor size is not observed in the feeding period (see FIG. 6).

2. Suppression Ratio of Tumor

Figure 7:
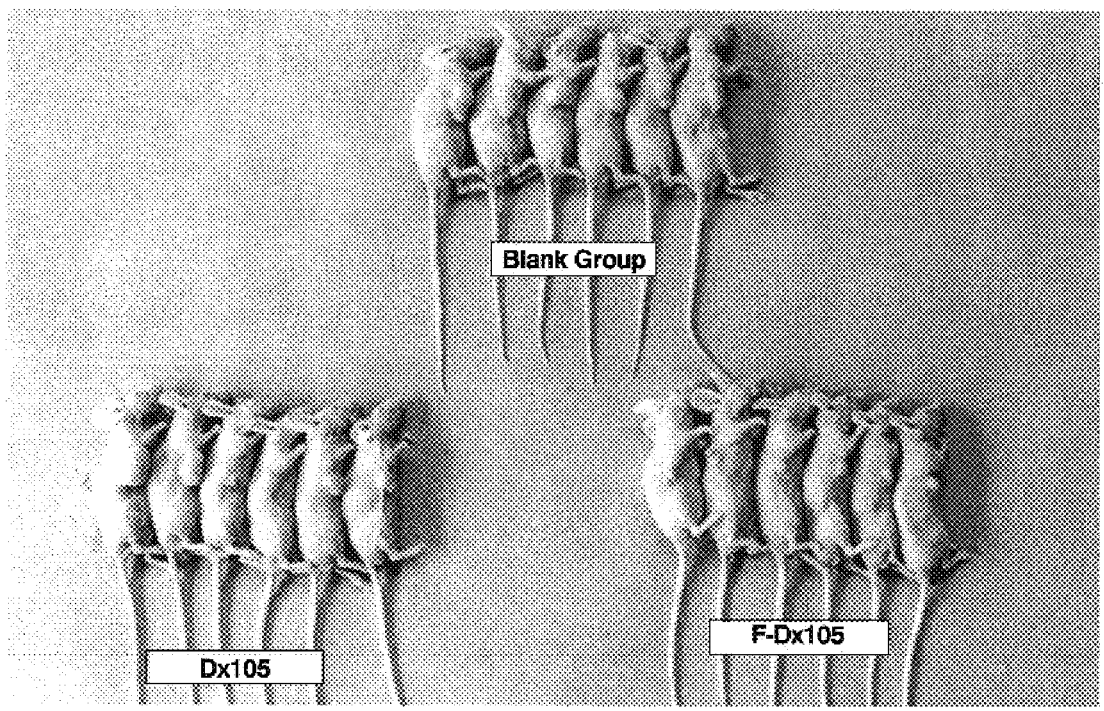
FIG. 7 shows: the comparison of tumor sizes in vivo of killed three groups of naked chmices having tumor, which are inoculated with HeLa229 cells and administering for 33 days (upper figure: blank group; lower left figure: Dx105; lower right figure: F-Dx105).
Figure 8:
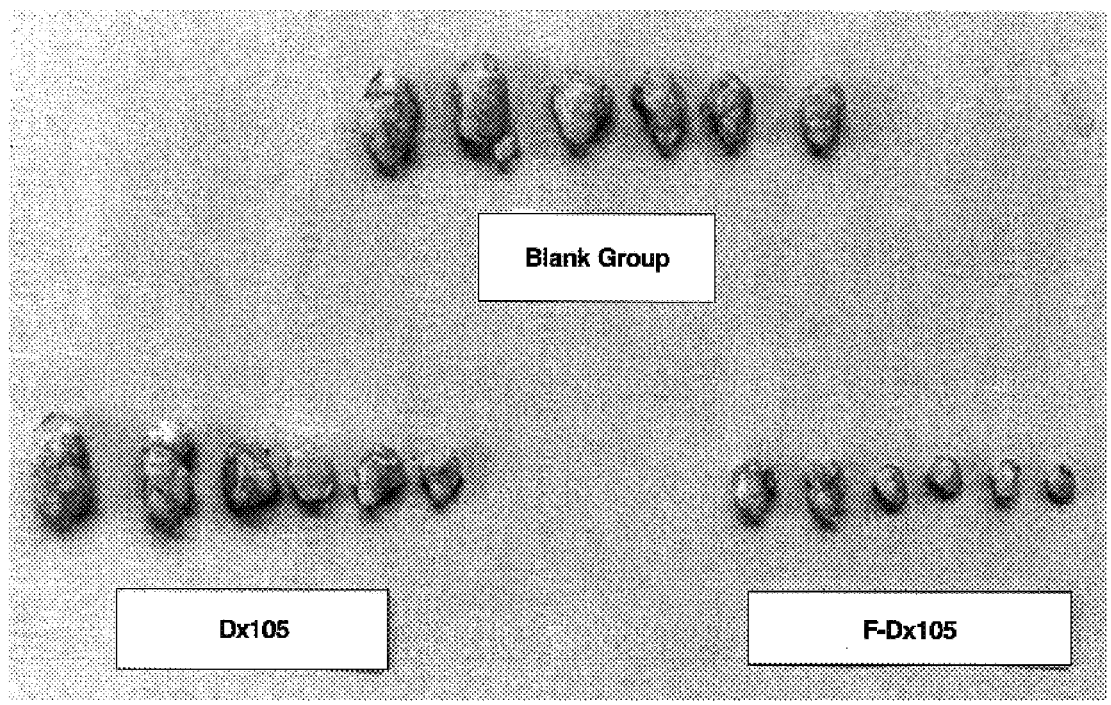
FIG. 8 shows: the comparison of tumor sizes in vitro of killed three groups of naked chmices having tumor, which are inoculated with HeLa229 cells and administering for 33 days.

The three groups of naked chmices having HeLa229 tumors are killed on the $33^{th}$ day after starting of administering (see FIG. 7), and the tumors are taken out and weighed (see FIG. 8). The suppression ratio of tumor is calculated by formula: [1−(tumor weight of experimental group/tumor weight of blank group)]×100%. The results show that F-Dx105 has the suppression ratio of tumor of above 70%, while Dx105 exhibits no notable suppression ratio of tumor (see the following table).

| Group | Number of animals (begin/end) | Weight of tumor (mg) | Suppression ratio of tumor (%) |
|---|---|---|---|
| Blank | 6/6 | 393.6 ± 201.6 | — |
| Dx105 | 6/6 | 416.1 ± 286.7 | −1.03 |
| F-Dx105 | 6/6 | 98.4 ± 38.3 | 74.36 |

3. Observation of Morphology of Tumor Tissue

Figure 9A:
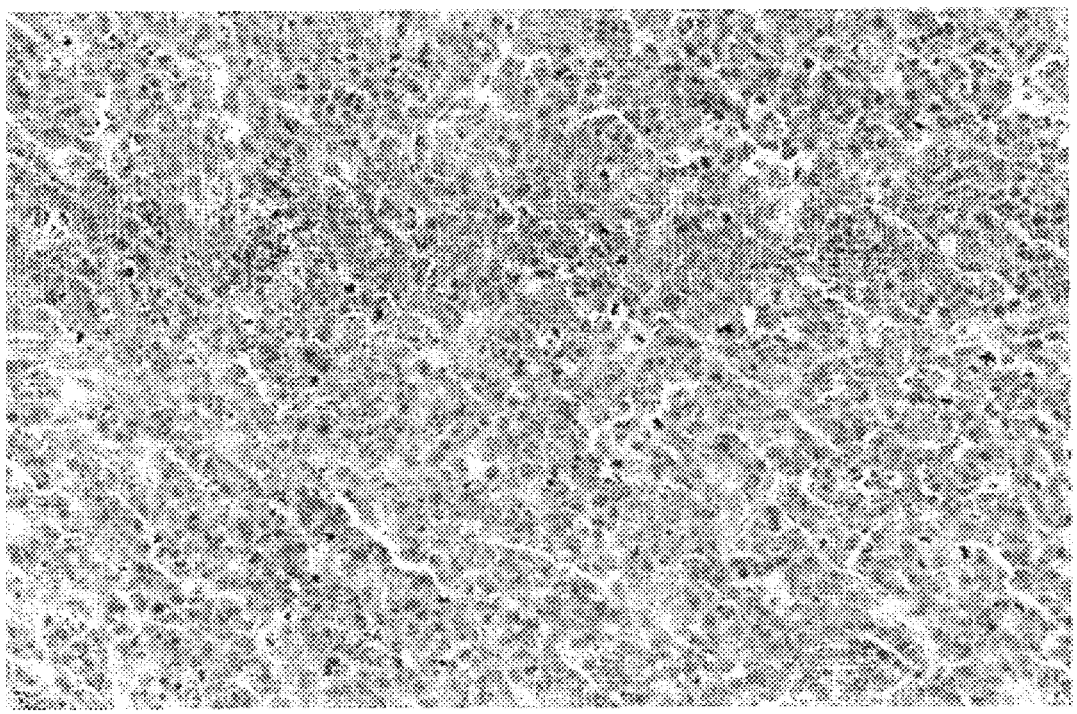
FIG. 9a shows: the tumor tissue slice of blank group of naked chmices having tumor, which are inoculated with HeLa229 cells and fed for 33 days.
Figure 9B:
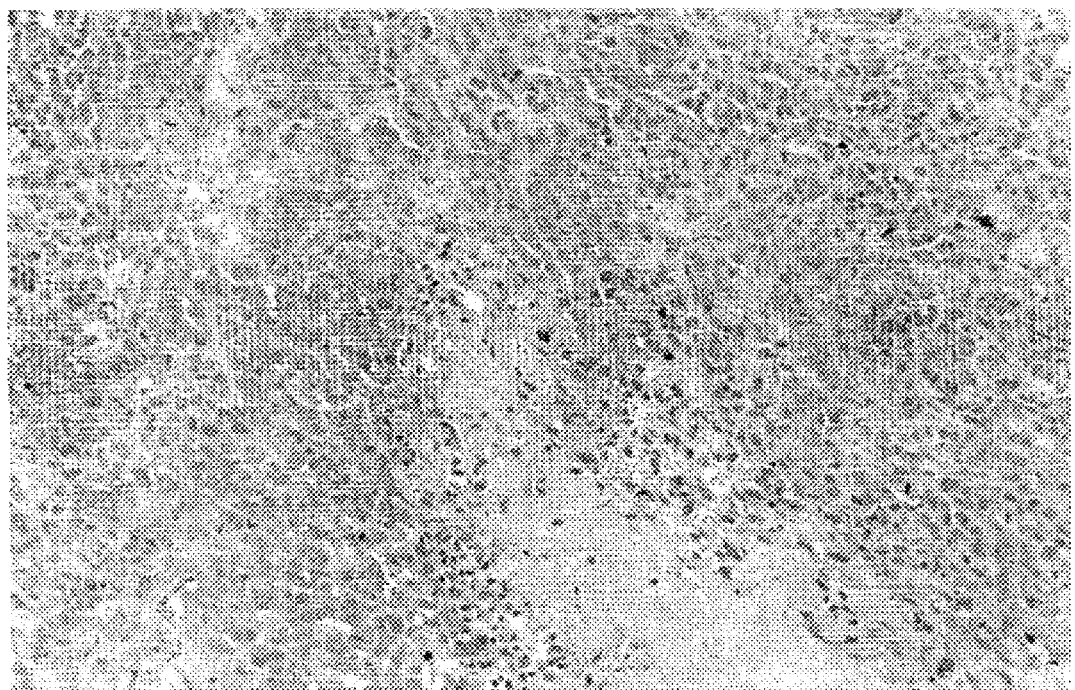
FIG. 9b shows: the tumor tissue slice of Dx105 group of naked chmices having tumor, which are inoculated with HeLa229 cells and administered for 33 days.
Figure 9C:
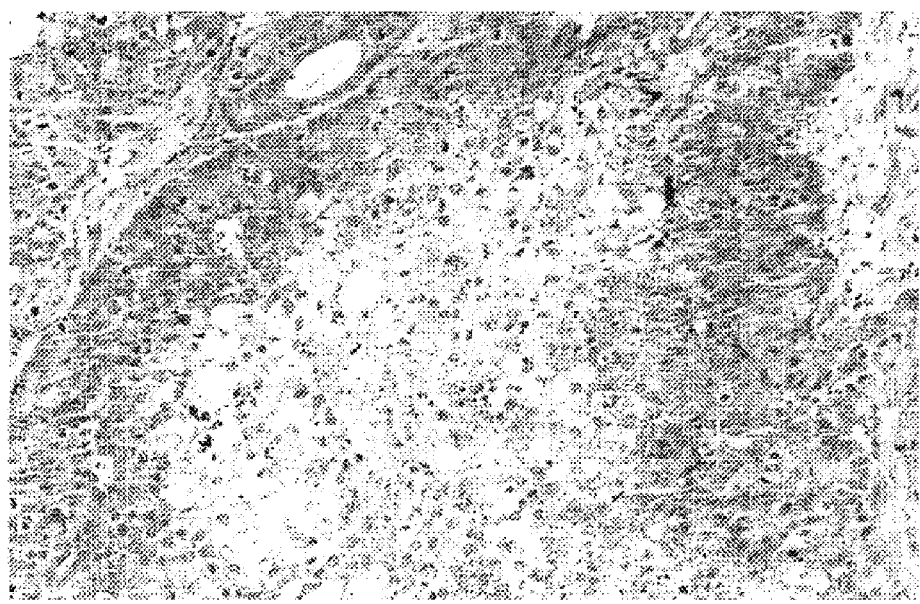
FIG. 9c shows: the tumor tissue slice of F-Dx105 group of naked chmices having tumor, which are inoculated with HeLa229 cells and administered for 33 days.

After fixing three groups of tumor tissues, the tumor tissue slices are obtained by conventional methods and sealed and fixed on glass slides, then they are observed and filmed by phase contrast microscope (see FIGS. 9a, 9b and 9c). The results showed that the tumor cells in tumor tissues of F-Dx105 group are dead or disintegrated in large amounts and many hollow vesicae exist in said tumor tissues, while only partial fiberosis and a small quantity of dead tumor cells are found in the tumor tissues of Dx105 group.

4. Determination of DNA Index of Tumor Cell in Tumor Tissue

After fixing three groups of tumor tissues, the 5 $\mu$m tumor tissue slices are obtained by gradient dewatering tumor tissues with ethanol, embedding with paraffin and cutting, and then they are placed on glass slides, dyed by improved Feulgen-azur A method, sealed and fixed. DNA contents of 50 tumor cells and iymphocute cells (as normal cells) of each of tissue slices are measured by the Image Cytometer, CAS-200. The DNA index (DI; the more DI is near 1, the more malignant extent of tumor cell is lower, or the more curative effect is better) of tumor cell in tumor tissue is calculated by the following formula.

$$DI = \frac{\text{DNA content of measured tumor cells}}{\text{DNA content of measured normal cells}}$$

The results show that the DI values of F-Dx105 group and Dx105 group are 66% and 89% of DI value of blank group (see the following table).

| Group | Slices | DNA mass of main peak (mg) | DI |
|---|---|---|---|
| Blank | 6 | 25.59 ± 2.95 | 3.51 ± 0.33 |
| Dx105 | 6 | 22.35 ± 0.58 | 3.11 ± 0.08 |
| P-Dx105 | 6 | 16.74 ± 0.83 | 2.33 ± 0.12 |

EXAMPLE 6

Toxicity Testing of F-Dx105 on Chmice

20 Kunming species chmices (2022 g) are divided into male group (10 chmices) and female group (10 chmices). Before administering, they are not fed for 3 hours, and weighed They are intravenously injected F-Dx105 (concentration of 50 mg/ml) in vena caudalis with administering dose of 1500 mg/kg and injecting volume of 0.3 ml/10 g. After administering, the appearance, activity, behavior and number of toxic chmice are observed everyday, and all chmices are killed after 7 days and their main visceral organs are examined. The results show that these chmices have no paradoxical reaction in one week, their body weight increase, no chmice is dead, and no abnormity is found in their main visceral organs, after intravenously injecting 1500 mg/kg of F-Dx105.

EXAMPLE 7

F-Dx105 Compositions

1 Lyophilized composition

Under stirring condition, 1.25 g F-Dx105 is dissolved in water for injection, and then diluted to 25 ml to obtain 50 mg/ml solution. Each 10 ml bottle is filled with 2 ml said solution, and lyophilized in lyophile apparatus for 48 hours to obtain lyophilized product having loose and flocculent form, and the product is packed in said bottle by adding a plug and sealing with aluminum cover.

2. Dry Syrup Composition (1) 33.0 g Folic acid-Dextran, 7.49 aluminum hydroxide and 3.2 g magnesium trisilicate are mixed sufficiently and poured into 10 bottles with volume of 150 ml. When being used, 100 ml warm water is added into each bottle, and shaken to obtain a suspension.

(2) 33.0 g Folic acid-Dextran and 5.0 g sodium hydrogen carbonates are mixed sufficiently and poured into 10 bottles with volume of 150 ml. When being used, 100 ml warm water is added into each bottle, and shaken to obtain a solution.

3. Enteric Capsule Composition 10.0 g Folic acid-Dextran and 0.2 g magnesium stearate are mixed sufficiently and poured into 1# enteric capsule, where each capsule contains 100 mg folic acid-Dextran.

What is claimed is:

1. A folic acid-polysaccharide complex, characterizing in that it has the following general formula: (X)n-Y, wherein X is identical or different, and is selected from the group consisting of folic acid, folinic acid, dihydrofolic acid, tetrahydrofolic acid, tetrahydropterin, pteroyl-polyglutamic acid, 2-deamino-hydroxy-folic acid, 1-denitrofolic acid, 3-denitrofolic acid, 8-denitrofolic acid; and Y is a polysaccharide other than arabinogalactan selected from glucans, dextrans, polysaccharoses, frustosans, heteropolysaccharides, mono- or heteropolysaccharide sulfates, mono- or heteropolysaccharide polysaccharides, ginseng pectin polysaccharide and other pectic polysaccharides, gummi tragacanthae, gumghatti, alginate, mono- or hetero-glycuronate-polysaccharides, polyethylene oxide, methoxypolyethylene glycol, and hydrophilic alcoholic polymers; and $n \geq 1$; wherein said folic acid-polysaccharide complex enters into cell via the pathway of the folic acid receptor on the cell membrane.

2. A folic acid-polysaccharide complex according to claim 1, characterizing in that said polysaccharide Y is selected from the group consisting of glucans, polysaccharoses, fructosans, heteropolysaccharides, mono- or heteropolysaccharide sulfates, mono- or hetero-glycuronate-polysaccharides and other hydrophilic alcoholic polymers.

3. A folic acid-polysaccharide complex according to claim 2, characterizing in that said polysaccharide has the molecular weight range of 4,000 to 2,000,000.

4. A folic acid-polysaccharide complex according to claim 2, characterizing in that said glucans is dextran.

5. A folic acid-polysaccharide complex according to claim 4, characterizing in that said dextran has molecular weight range of 10,000 to 2,000,000.

6. A folic acid-polysaccharide complex according to claim 5, characterizing in that said dextran has molecular weight range of 10,000 to 150,000.

7. A folic acid-polysaccharide complex according to claim 6, characterizing in that said dextran has molecular weight of about 105,000.

8. A pharmaceutical composition useful in antineoplastics, characterizing in that it comprises folic acid-polysaccharide complex according to claim 1 and pharmaceutical acceptable adjuvants.

9. A pharmaceutical composition according to claim 8, characterizing in that it is in form of a lyophilized powder, dry syrup or enteric capsule.

10. A method for the treatment of tumor cells, on the cell membranes of which exist over-expressed folic acid receptors, in a patient in need thereof comprising the step of administering to the patient the folic acid-polysaccharide complex of claim 1.

11. A folic acid-polysaccharide complex according to claim 1, characterizing in that said polysaccharide has the molecular weight range of 4,000 to 2,000,000.

12. A folic acid-polysaccharide complex, characterizing in that it has the following general formula: (X)n-Y, where X is folic acid, Y is dextran, and $n \geq 1$.

13. A folic acid-polysaccharide complex, characterizing in that it has the following general formula (X)n-Y, where X is folic acid, Y is ficoll, and $n \geq 1$.

14. A folic acid-polysaccharide complex, characterizing in that it has the following general formula (X)n-Y, where X is folic acid, Y is dextrin, and $n \geq 1$.

15. A folic acid-polysaccharide complex, characterizing in that it has the following general formula (X)n-Y, where X is folic acid, Y is heparin, and $n \geq 1$.

16. A folic acid-polysaccharide complex according to claim 1, where X is dihydrofolic acid and Y is dextran.

17. A folic acid-polysaccharide complex according to claim 1, where X is tetrahydrofolic acid and Y is dextran.

* * * * *

UNITED STATES PATENT AND TRADEMARK OFFICE
CERTIFICATE OF CORRECTION

PATENT NO.         : 7,005,426 B2
APPLICATION NO. : 10/274854
DATED              : February 28, 2006
INVENTOR(S)        : Weiyue Lu et al.

It is certified that error appears in the above-identified patent and that said Letters Patent is hereby corrected as shown below:

Title Page #73
An Assignee has been omitted. Please insert:

-- Fudan University, Shanghai, China --.

Signed and Sealed this

Twenty-seventh Day of March, 2007

JON W. DUDAS
*Director of the United States Patent and Trademark Office*